United States Patent [19]

Kuipers

[11] Patent Number: Plant 7,657

[45] Date of Patent: Sep. 24, 1991

[54] SPATHIPHYLLUM PLANT NAMED GIGANT

[75] Inventor: Nico J. Kuipers, De Kwakel, Netherlands

[73] Assignee: Reginald Deroose, Belgium

[21] Appl. No.: 520,355

[22] Filed: May 7, 1990

[51] Int. Cl.[5] ..... A01H 5/00

[52] U.S. Cl. ..... Plt./88

[58] Field of Search ..... Plt./88

*Primary Examiner*—Howard J. Locker

*Attorney, Agent, or Firm*—Foley & Lardner

[57] ABSTRACT

A distinct Spathiphyllum plant named Gigant characterized by its large, strong, upstanding leaves that have all veins strongly impressed on the upper surface, numerous side shoots resulting in a full plant, very strong flowers and leaf stems, and its large white flowers.

2 Drawing Sheets

The present invention comprises a new and distinct cultivar of Spathiphyllum, botanically known as Spathiphyllum and referred to by the cultivar name Gigant.

The new cultivar is a product of a planned breeding program, and was originated from a cross made by the inventor during such a program in De Kwakel, The Netherlands in 1988.

The female, or seed pollen parent was an unnamed and presently unknown seedling. The male, or pollen parent was likewise an unnamed and presently unknown seedling.

Gigant was discovered and selected as a flowering plant within the progeny of the stated cross by the inventor on Aug. 9, 1988, in a controlled environment in De Kwakel, The Netherlands. Subsequent asexual reproduction by tissue culture has demonstrated that the combination of characteristics as herein disclosed for the new cultivar are firmly fixed and are retained through successive generations of asexual reproduction.

The following traits have been repeatedly observed and in combination distinguish Gigant as a new and distinct cultivar:

1. Large, very strong, upstanding leaves which are relatively wide (approximately 20 cm in the area of greatest width) in comparison with their length (approximately 30 cm).

2. Side shoots are numerous which gives the plant a large appearance.

3. The plant is tall, being approximately 90 cm in height when fully mature.

4. Flowering is regular and uniform. The flowers are very large and a beautiful white. The flowers when fully open extend up to 10–11 cm in width and 17–20 cm in length.

5. Very strong flower and leaf stems.

6. The leaves are dark green. Every vein is impressed on the upper surface, causing an uneven and bumpy effect.

The following observations, measurements and values describe plants grown in De Kwakel, The Netherlands under greenhouse conditions which closely approximate those generally used in horticultural practice. Color references are made to The Royal Horticultural Society (R.H.S.) Colour Chart, except where general color terms of ordinary significance are used. The color values were determined between 8:30–9:00 on Nov. 6, 1989 under bright but slightly cloudy daylight at Aalsmeer, The Netherlands.

In the color photographic drawings,

Sheet 1 comprises a front view of Gigant grown in a 17 cm pot.

Sheet 2 comprises a top photograph illustrating in more detail the shape and size of the spathe and spadix, and a bottom photograph illustrating the large leaves. Colors are as close as reasonably possible to obtain with color illustrations of this type.

The new cultivar can be compared to the Spathiphyllum cultivar Palace. Similarities are flower shape, flower color, and height. The new cultivar differs from Palace in that the leaves of Gigant are stronger, the leaves of Palace are shorter and narrower (approximately 12 cm wide and 27 cm long), and the veins of the leaves of Palace are not uniformly impressed in the upper surface. In addition, the flower and leaf stems of Palace are not as strong.

Classification:

*Botanical.*—Spathiphyllum cv Gigant.

*Commercial.*—Spathiphyllum.

Parentage:

*Male parent.*—Unnamed seedling.

*Female parent.*—Unnamed seedling.

Propagation: Vegetative propagation by tissue culture is preferred.

Plant: If plants are potted (at 4 to 5 months old) in 10 cm pots, at the time of first flowering (4 to 5 months after potting), the plant is 50–55 cm tall, measured from the top of the pot. If plants are repotted in 14–17 cm pots, the plants are 65–70 cm tall when second flower appears (six to eight weeks after that), and 85–90 cm tall when third flower appears (six to eight weeks later). Such height is then maintained. The plant is approximately 50 cm in diameter at its widest point.

*Growth habit.*—Vigorous, with many side shoots being produced. After the first flower appears 3 to 6 shoots are produced. As the plant continues to bloom, more side shoots are provided.

Leaves:

*Form and size.*—Elliptic, slightly asymmetrical. Length: Approximately 30 cm. Width: Approximately 19 cm.

*Texture.*—Leathery, upper surface is glossy.

*Veins.*—Strongly impressed on the upper surface.

*Color.*—Upper surface: Between 147A and 137A. Lower surface: Slightly greener than 147B.

Flowers:

*Buds.*—Formed in leaf axil.

Spathe:

*Size.*—Approximately 15 cm long and 9 cm wide.
*Color* (*R.H.S.*).—155D.
*Arrangement.*—Extends erect from the flower stem.
*Shape.*—Oval.
*Flowering.*—Regular, uniform.

Spadix:
*Size.*—5-7 cm in length.
*Color* (*R.H.S.*).—158B.
*Longevity.*—2 to 3 months.

Reproductive organs:

*Stamens.*—White, normal.
*Anthers and filaments.*—White, normal.
*Pollen.*—White, normal.
*Pistils.*—White, normal.

Roots: White in color; normal root system.

Disease resistance: No disease problems noted to date.

I claim:

1. A new and distinct Spathiphyllum plant named Gigant, as described and illustrated.

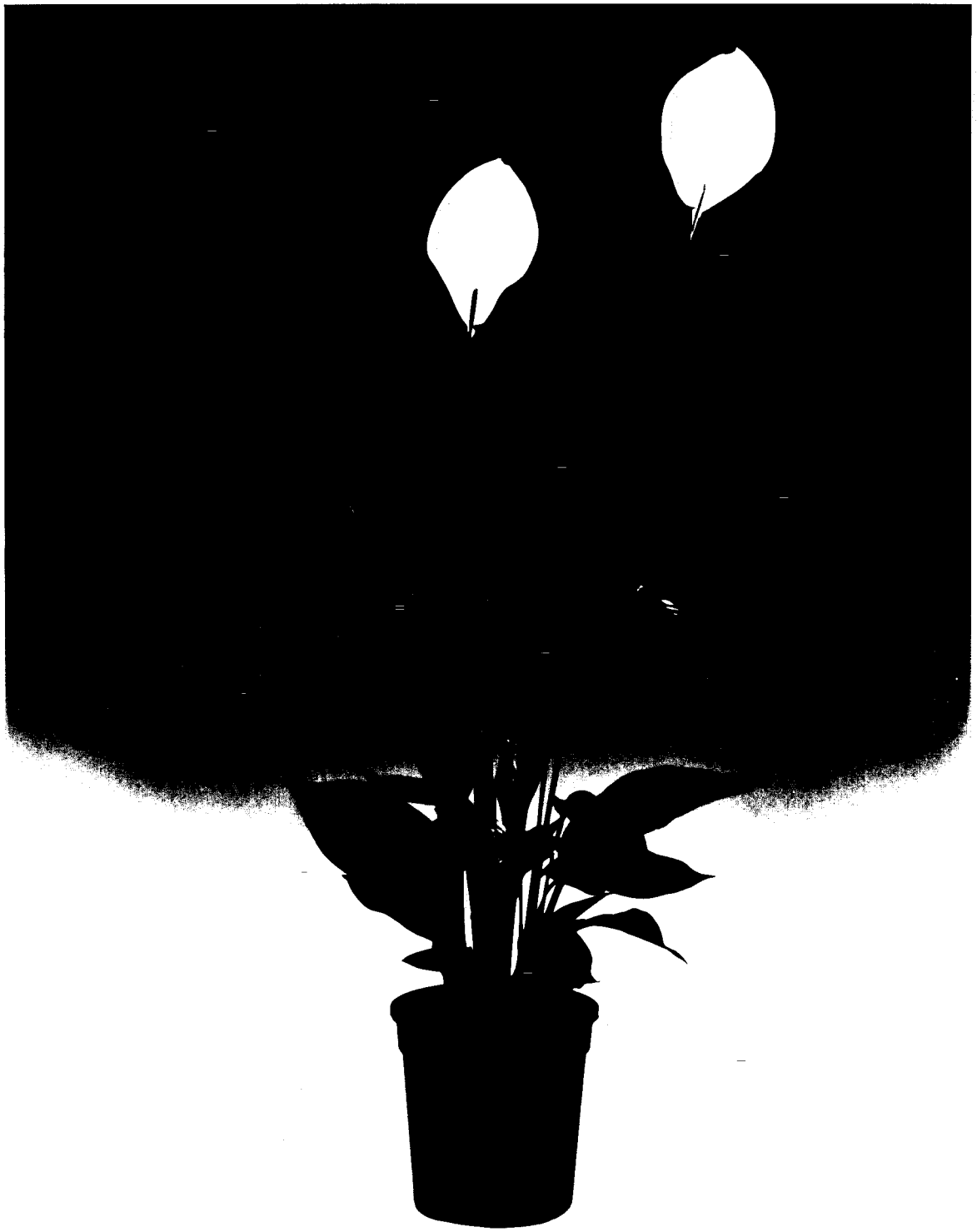

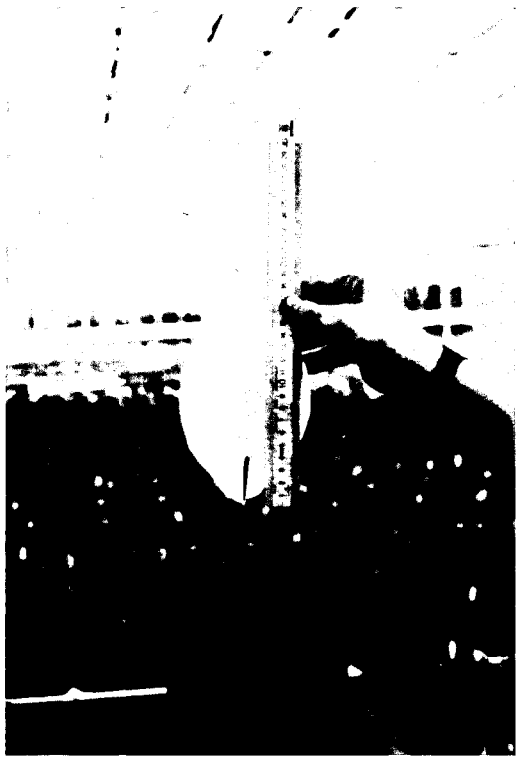
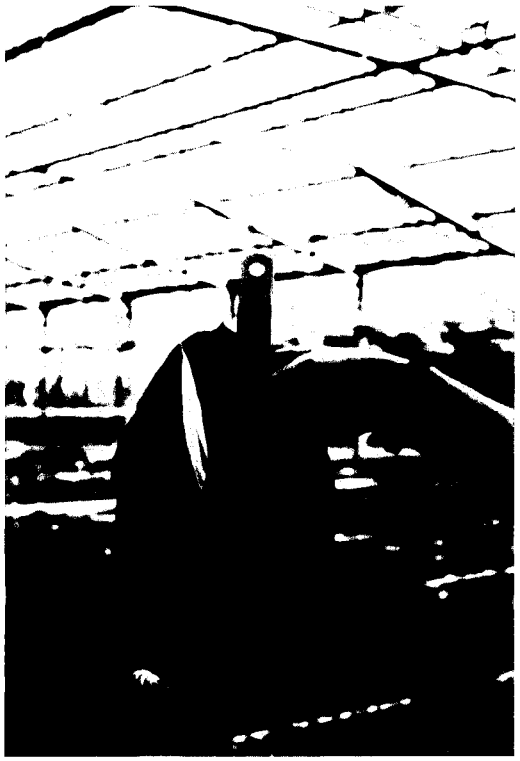

* * * * *